United States Patent [19]
Jacobson et al.

[11] Patent Number: 5,382,248
[45] Date of Patent: Jan. 17, 1995

[54] SYSTEM AND METHOD FOR STABILIZING BONE SEGMENTS

[75] Inventors: Robert E. Jacobson, Coral Gables; Brian J. Mirson, Miami, both of Fla.

[73] Assignee: H. D. Medical, Inc., Miami, Fla.

[21] Appl. No.: 944,206

[22] Filed: Sep. 10, 1992

[51] Int. Cl.[6] ............................................. A61B 17/56
[52] U.S. Cl. ........................................ 606/60; 606/61; 606/73
[58] Field of Search .................. 606/60, 61, 72, 73, 606/54-59

[56] References Cited

U.S. PATENT DOCUMENTS

| | | | |
|---|---|---|---|
| 4,244,360 | 1/1981 | Dohogne | 128/92 A |
| 4,308,863 | 1/1982 | Fischer | 128/92 A |
| 4,360,012 | 11/1982 | McHarrie et al. | 128/92 EB |
| 4,611,582 | 9/1986 | Duff | 606/61 |
| 4,624,249 | 11/1986 | Alvarez Cambras | 128/92 ZK |
| 4,805,602 | 2/1989 | Puno et al. | 128/69 |
| 4,854,304 | 8/1989 | Zielke | 606/61 |
| 4,913,134 | 4/1990 | Luque | 128/69 |
| 4,941,481 | 7/1990 | Wagenknecht | 606/59 |
| 4,946,458 | 7/1990 | Harms et al. | 606/61 |
| 4,957,495 | 9/1990 | Kluger | 606/58 |
| 4,988,349 | 1/1991 | Pennig | 606/58 |
| 5,005,562 | 4/1991 | Cotrel | 128/69 |
| 5,047,029 | 9/1991 | Aebi et al. | 606/61 |
| 5,053,034 | 10/1991 | Olerud | 606/61 |
| 5,084,049 | 1/1992 | Asher et al. | 606/61 |
| 5,085,660 | 2/1992 | Lin | 606/73 |
| 5,152,303 | 10/1992 | Allen | 128/898 |
| 5,176,679 | 1/1993 | Lin | 606/61 |
| 5,209,753 | 5/1993 | Biedermann | 606/72 |
| 5,234,431 | 8/1993 | Keller | 606/61 |
| 5,254,118 | 10/1993 | Mirkovic | 606/61 |

FOREIGN PATENT DOCUMENTS

| | | | |
|---|---|---|---|
| 0452792 | 10/1991 | European Pat. Off. | 606/61 |
| 2612070 | 9/1988 | France . | |
| 216625 | 12/1984 | German Dem. Rep. . | |
| 3244819 | 6/1984 | Germany . | |
| 3841008 | 6/1990 | Germany | 606/61 |
| 0848009 | 7/1981 | U.S.S.R. | 606/61 |

OTHER PUBLICATIONS

J. T. Merenda, A. Moskowitz, B. Akbarnia, A. Carl, P. Niemann and B. Measeck; "Surgical Treatment of Spine Fractures Using Cotrel-Dubousset Instrumentation"; copyright 1987, 1989; pp. 1-21 and inserts.

Wiltse; Advanced Spine Fixation Systems Incorporated; chapter entitled, "the Wiltse Pedicle Screw Fixation System;" pp. 1-26.

(List continued on next page.)

*Primary Examiner*—Michael A. Brown
*Attorney, Agent, or Firm*—Pennie & Edmonds

[57] ABSTRACT

An apparatus for stabilizing a plurality of bone segments, such as vertebrae of a spinal column, comprises one or more fixation devices. Each fixation device comprises an elongated rod having a longitudinal slot through its upper and lower surfaces and having threaded lateral surfaces. Slotted or axially threaded block members are slideably or rotatably movable along each rod into predetermined positions corresponding to locations selected for securing the apparatus to the bone. Posts are provided having have threaded distal ends, such that the distal end of each such post is inserted into the bone. The proximal end of each post is passed through the longitudinal slot in the rod and also through a vertical bore in the block member. The locations at which corrective forces are applied by the posts may be changed relative to the rods in three planes. A transverse connector system, included when at least two implant sets are used permits the implant sets to be spaced different distances apart and at different angular orientations.

24 Claims, 8 Drawing Sheets

OTHER PUBLICATIONS

B. Akbarnia, R. Gaines, Jr., L. Keppler, M. Lorenz, M. Zindrick and P. Niemann; "Surgical Treatment of Fractures and Fracture Dislocations of Thoracolumbar and Lumbar Spine Using Pedicular Screw and Plate Fixation;" 1988; 6 page report.

J. Zucherman, K. Hsu, A. White and G. Wynne; "Early Results of Spinal Fusion Using Variable Spine Plating System;" Dec. 8, 1987; pp. 570–579.

A. D. Steffee and L. Keppler; "VSP Plating System Technique Manual;" pp. 1–14.

P. M. Lin and K. Gill; Lumbar Interbody Fusion: Principles and Techniques in Spine Surgery; chapter entitled "The Variable Screw Placement System and Posterior Lumbar Interbody Fusion;" 1989; pp. 81–93.

Danek Medical, Inc.; "TSRH Crosslink;" 1987; 6 page pamphlet.

E. R. Luque; Surgical Technique; "Interpeduncular Segmental Fixation (I.S.F.);" Apr. 1989; 9 page presentation.

C. C. Edwards; "A Modular Spinal System;" 8 page report.

J. Zucherman, K. Hsu, A. White and G. Wynne; "Early Results of Spinal Fusion Using Variable Spine Plating System;" Dec. 1987; pp. 571–579.

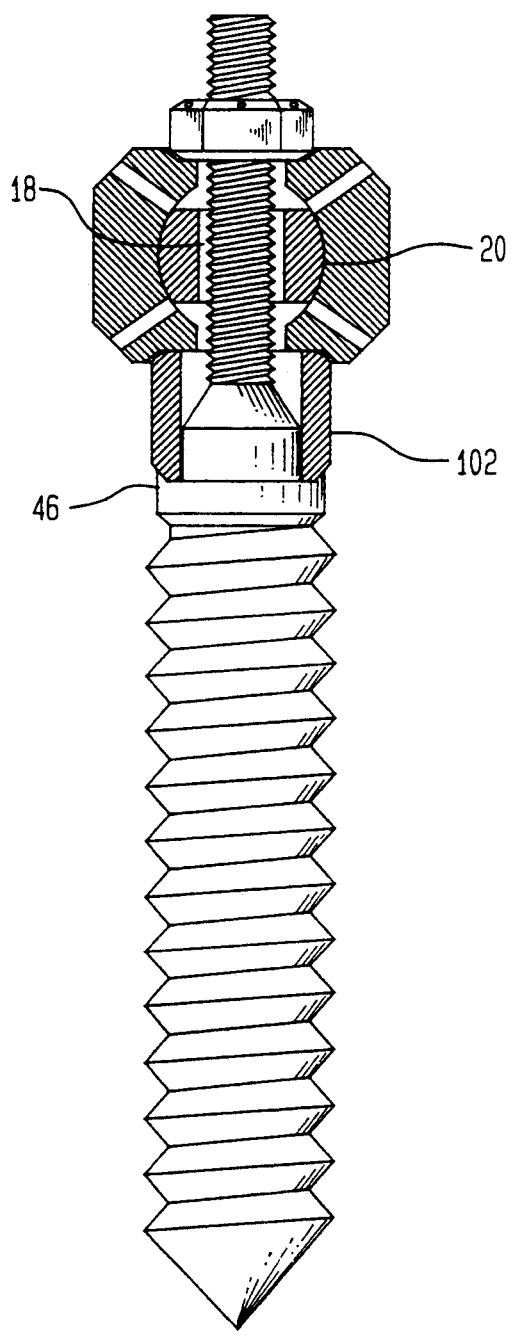

SYSTEM AND METHOD FOR STABILIZING BONE SEGMENTS

BACKGROUND OF THE INVENTION

1. Technical Field

The present invention relates generally to a system and method for stabilizing and immobilizing a plurality of adjacent bone segments. A typical, but non-limiting application of this system is in the field of posterior spinal fixation wherein a single system can be readily adapted for simple stabilization of adjacent vertebra or to effect the controlled angulation needed for reduction and distraction.

2. Description of the Prior Art

Posterior spinal stabilization systems are typically used for the treatment of conditions involving vertebral displacement such as kyphosis, spondylolisthesis and rotation; segmental instability, such as disc degeneration and fracture caused by disease, trauma, and congenital defects; and tumor diseases. The preferred method of spinal stabilization is immobilization of the affected joint(s) by surgical fusion, or arthrodesis. In order to permit fusion of adjacent vertebrae, immediate immobilization of any affected joints is necessary, which is preferably performed by internal fixation.

Internal fixation refers to methods of stabilization which are wholly internal to the patient and which include commonly known appliances such as bone plates or rods, hooks, and screws. Internal fixation is now the favored means of immobilization since the lack of external components allows the patient greater freedom of movement and reduces the possibility of infections. Prior art devices for internal posterior spinal fixation generally incorporate one of two basic design developments, top loading transpedicular plate systems and side loading elongated rod distraction/compression fixation systems.

Transpedicular plate systems comprise one or more parallel elongated plates having spaced apertures or longitudinal slots through which pedicle screws may be received and secured by appropriate fastening devices. The pedicles are a favored area of attachment upon the vertebrae since they offer an area of sufficient size, depth, and strength to hold the fixation device. Transpedicular screw and plate systems rely on a screw threaded into a reamed canal generally positioned perpendicular to the longitudinal axis of the spine and horizontal or parallel to the anterior/posterior plane of the vertebral body. Methyl methacrylate is sometimes used to secure the screw in the canal, particularly if the screw loosens or osteoporosis is a problem. The screws engage a plate which has been bent to conform to the normal curvature of the spine or to the points of desired reduction.

A transpedicular screw and plate system developed by Roy-Camille utilizes plates having spaced, predrilled holes. The pedicles are located, reamed, tapped, and two screws are inserted into each vertebral body. Corticocancellous bone graft is placed in the lateral gutter over the transverse processes. The upper portion of each screw is threaded and extends through a respective hole in the plate, being held there by a corresponding nut. This simple system was "top loading" in that it allows the surgeon to tighten all appliance connections through the center of the plate and from the top. However, although the Roy-Camille system immobilized or fixated the spinal segments, it provided minimal ability to apply any corrective forces thereto and forced the screw into a non-anatomic position to conform to the preformed holes.

A later top loading system, developed by Steffee, is known as the Variable Spinal Plate (VSP) system. Using the Steffee system, screws are inserted into the pedicles as described above. Slotted plates are contoured to a desired sagittal curvature and placed over the screws, following which tapered nuts are threaded onto the screws. The screws are then tightened bilaterally until the plate is locked between two nuts. The VSP system allows some limited application of corrective forces to the vertebrae along both axial and vertical directions but does not permit controlled angular positioning of the pedicle screws. Thus one drawback of the VSP system is that it is limited to fixation in two planes.

U.S. Pat. No. 5,084,049 to Asher et al. discloses a transpedicular plate system which permits fixation in three planes by using a transverse connector member to maintain the two slotted plates in a selected spaced relationship. Clamps at opposite ends of the transverse connector secure respective slotted plates at a desired angular orientation with respect to the horizontal plane. The Asher system, however, does not permit the surgeon to vary or control the angulation of the screws segment by segment, and it is not top loading in that the transverse connector requires tightening of set screws from the side.

A significant drawback of the above described slotted plate systems is that the risk of pedicle screw breakage is increased because of the need to conform the plates to sagittal curvature by bending. Specifically, to the extent that the angle of a screw varies from a perpendicular relationship to the portion of the plate to which it is affixed, the screw will be forced to either bend or seat in a position which generates constant torque. Variance from a perpendicular relationship may thus result in constant unidirectional torque of the screw against one wall of the pedicle, which may in turn cause weakening of the screw, erosion of the bone or undesirable shifting of the vertebrae-to-adjacent-vertebrae angular relationship.

Where treatment requires the introduction of corrective forces to the vertebrae at various transverse angles to the horizontal plane (i.e., reduction/distraction), present systems employ a system of elongated rods having circular cross sections. The circular cross section of the rods permits rotation of appliances which secure bone hooks or screws to the rod. Once the surgeon determines how much corrective force he wishes to apply to each vertebrae, the elongated rods of these systems are bent to achieve the desired spacing between the rod and each of the given vertebrae to be corrected. Combinations of hooks (laminar, pedicle, and transverse), sacral attachments (screws or rod extensions), or supporting wires are then connected to the rods at desired locations using the rotatable appliances. Examples of such systems include the Harrington distraction system sold by Zimmer USA, Inc., the Keene system shown in U.S. Pat. No. 4,269,178, and the Lewis-Greenlaw system illustrated in U.S. Pat. No. 4,085,744.

These systems are side loading in that the hooks and screws which are secured to the rod must be fastened along lines which are spaced from the longitudinal axis of the rod. Because of this spacing, the side-loading rod systems are more difficult to install than top-loading, slotted plate systems, especially where deep, angled incisions are involved (such as in fixation of the low lumbar spine).

Another drawback of the elongated rod systems is their susceptibility to rotational misalignment. Specifically, the aforementioned spacing between the longitudinal axis of the rod and the post attachment point creates a considerable risk of in situ rotational displacement because the reactive forces of the posts are directed about the center axis of the rods. The greater the spacing between the post connection point and the rod center axis, the greater the risk of rotational displacement of the rod.

The recently developed AMSET TM R-F system also utilizes threaded rods to effect segment by segment angular positioning of pedicle screws. Unlike the elongated rod systems discussed above, however, the R-F system also provides some of the benefits associated with the top loading slotted plate systems. To effect angular positioning relative to a vertical plane transverse to the longitudinal axis of the rod, the R-F system employs screws which have a unique U-shaped head design, wherein the threaded portion of the screw is available at angles of 0°, 5°, 10° and 15° relative to the head. The head defines a channel dimensioned to receive the threaded rod. Rotation of the head relative to the rod effects angular positioning relative to a horizontal plane. A pair of traction nuts engage respective faces of the head to maintain the screw in the desired orientation. When only simple fixation is required, the R-F system utilizes a specially machined block having a smooth vertical bore for receiving the upper threaded portion of a pedicle screw and a horizontal bore for sliding movement along the rod. Blocks are slid into desired positions along the rod to line up with inserted pedicle screws and are locked in place by pairs of traction screws. When the rod is installed, the respective blocks receive corresponding screws and nuts are tightened thereon to lock the rod into position.

Although the R-F system does provide an elongated rod system capable of providing both top loading simple fixation and selected segment by segment angular correction, it does not provide all of the benefits of the slotted plate system. Specifically, when used to provide simple fixation, it still suffers from the risk of unbalanced reactive forces as a result of the spacing between the axis of the rod and the post attachment points.

Thus, it should be apparent that in exchange for their ability to allow graded, angular movement at each segment, the elongated rod systems sacrifice the simplicity and rotational stability of slotted rod systems. Accordingly, unless the treatment requires segment by segment angular positioning of the screws, it will generally be more appropriate to use a slotted plate system.

Heretofore, the distinct advantages of the slotted plate systems and the elongate rod systems have required the surgeon to learn how to use a form of each system and the hospital to buy or have access to a variety of different systems, depending upon the preference of the surgeons practicing therein. Using the available systems of the prior art, the surgeon must preoperatively decide on the type of fixation treatment required and then chose an appropriate system to use. There has thus been a long felt need by those in this art for a single-system offering all the advantages of the prior systems, which may be adapted to a variety of differing operative conditions and applications, which also provides variable types of control at each level as needed.

SUMMARY OF THE INVENTION

The present invention thus presents a versatile new system capable of the simple, top loading fixation provided by the slotted plate systems and the selective angular correction provided by the elongated rod systems. Specifically, the system of the present invention can be used either as a simple slotted plate when that is sufficient or can accommodate a graded movement at any segment, as needed. A new post member design allows variable controlled angles and three plane adjustment.

The present invention is deemed to have general application in the stabilization of adjacent bone segments throughout the body of a patent and particular application to the stabilization of vertebrae in the thoracolumbar, lumbar, and sacral spine. For convenience therefore, the invention is described herein with reference to its use in spinal fixation, but this description should not be construed as limiting the invention to this particular application since the device described herein works equally well in stabilizing bones other than those in the spine.

There are problems of fixation unique to the lumbar area of the spine such as the fact that this area is normally lordotic and this lordosis must be preserved. In addition, there is a need to provide corrective forces in the case of a fracture or a deformity. Additionally, the points of sacral fixation are the weakest point of fixation and therefore require special accommodations. These problems are specifically addressed by the present invention.

The present invention is a device for the stabilization of one or more bone segments comprising, in one embodiment, a single fixation assembly as described below, i.e., for use with bones other than the spine, or alternately, in a further embodiment, two interconnected fixation assemblies for use in stabilizing and/or adjusting the bones of the spine. Each such assembly comprises an elongated rod member having a threaded exterior portion, said rod defining at least one slotted opening extending entirely therethrough from a first upper surface to a second lower surface thereof. The assembly further comprises at least two anchor means for securing the device to one or more bone segment(s). Each anchor means comprises a post member, having a threaded distal end for engaging a bone and a proximal end configured and adapted to extend through the opening in the rod and locking means engageable with the proximal end of said post member for locking the elongated rod to the post. In one embodiment, one or more of the post members may be "bent" i.e., having a portion thereof longitudinally offset or "angled" from the vertical, to provide the capability of variably angling the stabilization device of the invention as desired relative to the surface of the bone.

Each elongated rod comprises upper and lower surfaces through which the opening in the rod extends and first and second lateral surfaces which are externally threaded. Moreover, each post member comprises a shoulder portion located between its proximal and distal ends, which shoulder portion is positioned and adapted for engagement with a lower surface of said locking means. The assembly further includes a plurality of spacers. The spacers are engageable with the shoulder portion of the post member for controlling the distance between the shoulder portion and the lower surface of the locking means.

The locking means comprises a block nut member having both an axial opening and a vertical opening extending therethrough. The axial opening receives the elongated rod while the vertical opening of the block nut member receives the proximal end of a corresponding post member. The locking means further comprises means for retaining the proximal end of the post member after it has been received in the vertical opening of the block nut member and for retaining the post member in fixed relation with the block nut member, either perpendicularly or at an incremental angle.

In one embodiment of the present invention, the axial opening of the block nut member comprises a threaded bore. The block nut member is thus in threaded engagement with the elongated rod for rotatable movement therealong, wherein the threads provide a locking engagement between the rod and the block to prevent unwanted axial movement by the block along the rod. In one version of this embodiment, the axial opening intersects the vertical opening within the block nut member. In another version, the vertical opening is offset from the axial opening, i.e., they do not intersect.

In yet another embodiment, the axial opening is configured as a slot, i.e., it is not threaded, and the block nut member is thus slideably movable along the elongated rod. The locking means used with the subject embodiment thus further comprises means for securing said slotted block nut member in a predetermined position relative to said elongated rod. One example of such securing means comprises adjustable traction nuts positioned upon the rod on either side of and abutting against the block nut member to control movement of said member along the rod for permitting distraction or compression of the bone.

The present invention further includes means for maintaining a pair of said rod members in predetermined spatial relation to each other, said means comprising an elongate connecting member extendable between the rod portion of each fixation assembly, first attaching means for connecting a first portion of the elongate connecting member with a first one of the elongated rod members, and second attaching means for connecting a second portion of the elongate connecting member with the other elongated rod such that, by rotating the elongate connecting member, the action of cooperating threaded portions upon the attaching means and the elongate connecting member causes the elongated rod members to be drawn together or pushed apart, depending upon the direction of rotation which is chosen, i.e., clockwise or counterclockwise. The attaching means are preferably clamping assemblies, each comprising a pair of clamp members configured and adapted to work in unison for gripping engagement of both longitudinal sides of the elongated rod member. These clamp members are threaded to permit locking engagement with the threaded outer surface by the elongated rod.

The invention additionally includes end blocks positioned at a lower (i.e., adjacent the sacrum) terminal portion of the elongated rod for securing each said elongated rod to a patient's sacrum. Each end block defines a first aperture configured for receiving the elongated rod and a second aperture adapted for receiving a sacrum engaging screw which has a threaded distal portion similar to that of a post member but wherein the proximal portion is provided with a bolt head. The first aperture defines a first axis and the second aperture defines a second axis intersecting with the first axis, wherein the first and second axes intersect at an angle of between about 65 and 90 degrees.

The system of the invention additionally includes a bore adjustment member intended for use where (1) a post member for affixing a block nut member (either threaded or slotted) to a vertebra, or (2) a screw for attaching an end block to the sacrum, is broken or loosened from within its bore hole and therefore must be repaired or replaced. The bore adjustment member is interposed between the post (or the screw) and the corresponding bone, and is provided with an augur thread configuration upon its outer surface adapted to permit creation of a bore within the bone having a width greater than that of the originally emplaced post or screw.

A repair is thus effected by removing the damaged post or screw and twisting the bore adjustment member into the bone until the upper surface of the member lies flat upon the surface of the bone, after which a new post (or screw) is inserted into a threaded axial inner bore portion of the member having a pitch and a diameter corresponding to that of the threaded distal portion of the post or screw, whichever is used. The member may thus be provided in variety of different sizes to correspond to the dimensions of several different sized posts and/or screws used in a number of applications.

BRIEF DESCRIPTION OF THE DRAWINGS

FIG. 5 is a cross sectional view of a spacer situated between the block nut member and the bone screw shoulder of the embodiment of FIG. 1.

DETAILED DESCRIPTION OF THE INVENTION

Figure 1:
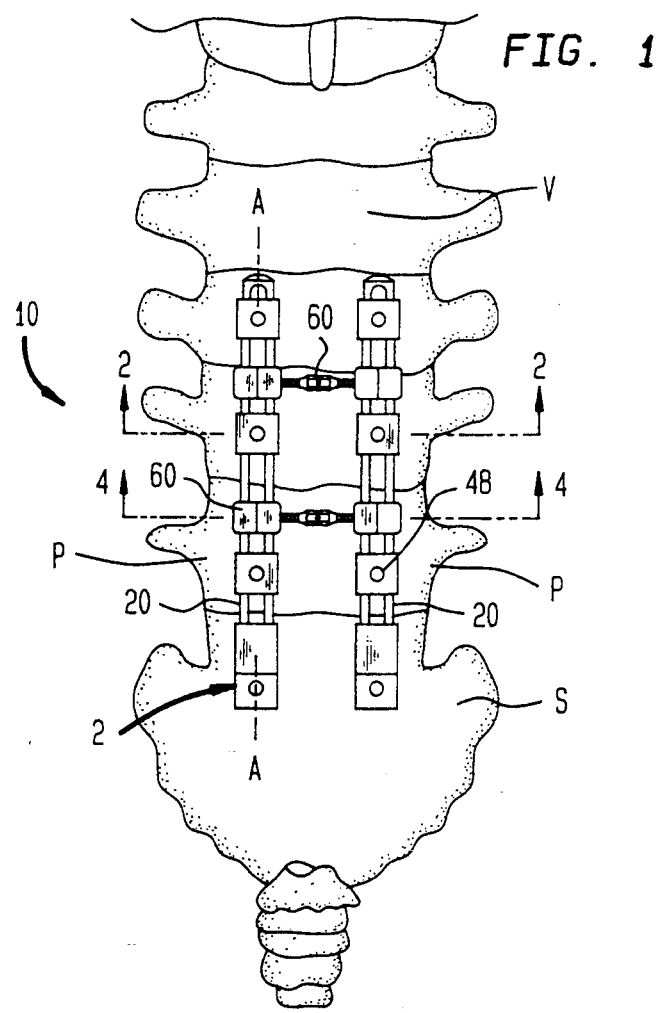
FIG. 1 is a plan view of one embodiment of the present invention.

One embodiment of the present invention is illustrated in FIG. 1. A portion of a spinal column is shown, including a plurality of vertebrae V and a sacrum S. The fixation device generally indicated at 10 includes a pair of rod members 20 which are connected to several vertebra V, at respective pedicle portions P thereof, to obtain the desired relative positions therebetween.

Each of the rod members 20 is elongate and has a length sufficient to span several vertebrae V which are to be immobilized. It will be readily appreciated that rod members 20 may either be substantially straight or, alternately they may be curved at a predetermined angle, although such curvature (in contrast to the prior art systems discussed above) is not required. In addition, rod members 20 are provided in a variety of lengths as required to achieve stabilization and application of correcting forces in a given area. It will also be apparent that the rod members 20 may be located anywhere along the bone segments to be immobilized and that the location illustrated in FIG. 1 is for illustrative purposes only.

Further, as previously noted, the system of the present invention may be used in a variety of applications for stabilizing, immobilizing and/or adjusting a plurality of bone segments located in a variety of locations within a patient's body, i.e., in addition to its use as a spinal fixation device. Thus the present description, which is provided only for purposes of illustration to assist in understanding the invention, should not be construed as limiting the use of the system only to spinal fixation.

Figure 3:
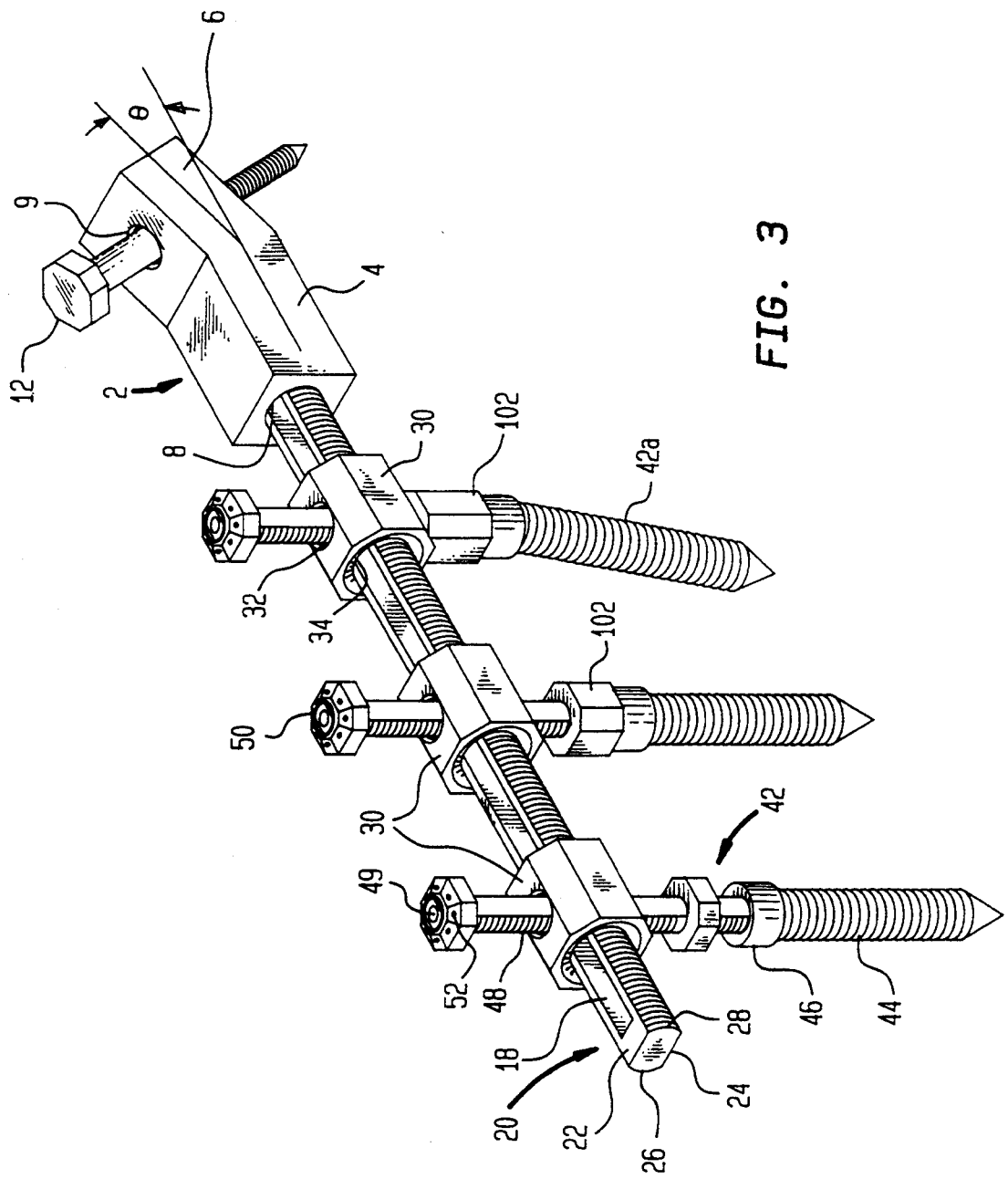
FIG. 3 is perspective view of the embodiment of FIG. 1.

As best shown in FIG. 3, the upper and lower surfaces 22 and 24, respectively, of each rod member 20 are planar, i.e. flat, and longitudinally continuous. The side surfaces 26 and 28 are arcuate and externally threaded. Although it is preferred that surfaces 26 and 28 be threaded along the entire length of rod member 20, it is contemplated that any arrangement of threaded and non-threaded sections might be used. For example, rods 20 might be provided, if desired, with an alternating arrangement of threaded and non-threaded segments along surfaces 26 and 28.

An elongated slot 18 extends through surfaces 22 and 24 of each rod 20. A single slot is preferred because it permits infinite adjustability along the length of the rod. However, any longitudinal arrangement of slots or other apertures is contemplated. For example, a plurality of slots may be provided in each rod at spaced intervals. These slots may be of constant or varying lengths as desired. Alternatively, a plurality of spaced vertical bores might also be used. In a preferred embodiment, rod members 20 are 8 mm in diameter with a 4 mm slot.

Adjustably positioned along the rod members are a plurality of block nut members 30. Each block nut member 30 has a vertical bore 32 and a threaded axial bore 34. The diameter and thread of the axial bore 34 corresponds to the external diameter and thread of the rod 20, as defined by threaded surfaces 26 and 28. When a block nut member 30 is properly positioned on the rod member 20, vertical bore 32 is aligned with slot 18. It should be apparent that the ability to move block nut members 30 along the rod permits the system to be adapted to fit any linearly spaced arrangement of fastener assemblies 40, as will be described below.

Figure 2:
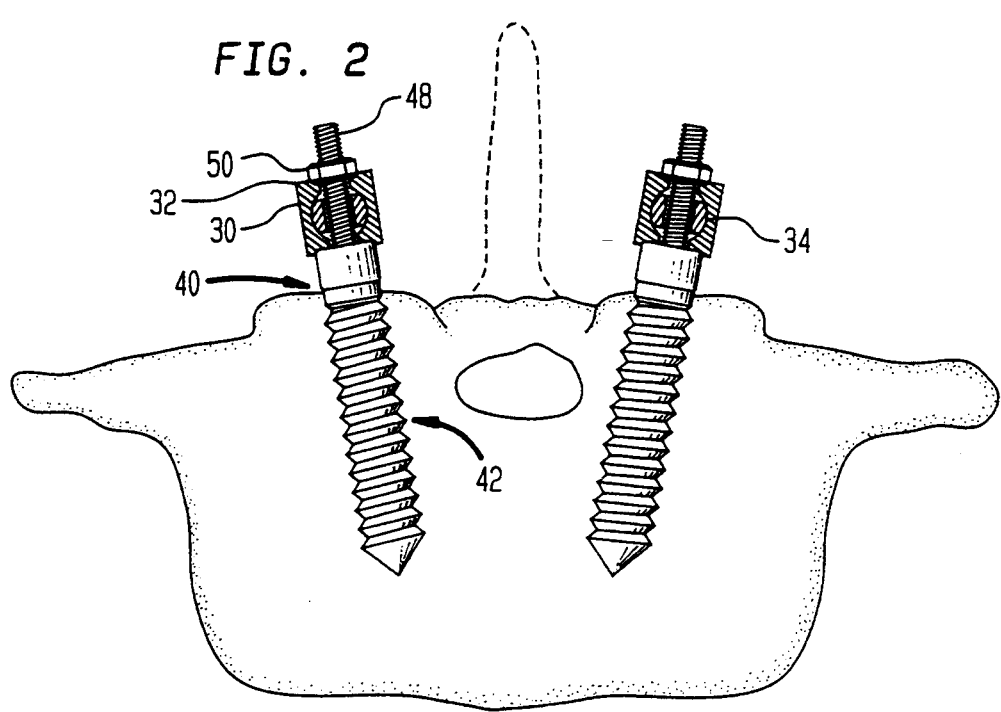
FIG. 2 is an enlarged cross sectional view of the embodiment of FIG. 1 connected to a vertebra, taken approximately along line 2—2 in FIG. 1.

The vertical bore 32 of block nut member 30 is configured to receive a fastener assembly 40, as illustrated in FIGS. 2 and 3, to connect each of the rod members to a pedicle P of the vertebra V. As best seen in FIGS. 2 and 3, each fastener assembly 40 includes a post member (also referred to herein as a "post") 42 having a threaded portion 44 (preferably in 6 mm and 7 mm diameters with varying lengths) threaded into a cancellous portion of the vertebra V. A shoulder 46 on the post spaces rod member 20 away from the vertebra V and provides for a smooth interface with the bone.

Post member 42 includes a second threaded portion 48 which extends through the slot 18 of rod member 20 and passes through vertical bore 32 in block nut member 30. Once rod 20 and block nut member 30 are penetrated by threaded portion 48, block 30 can no longer rotate and thereafter becomes fixed.

Figure 8:
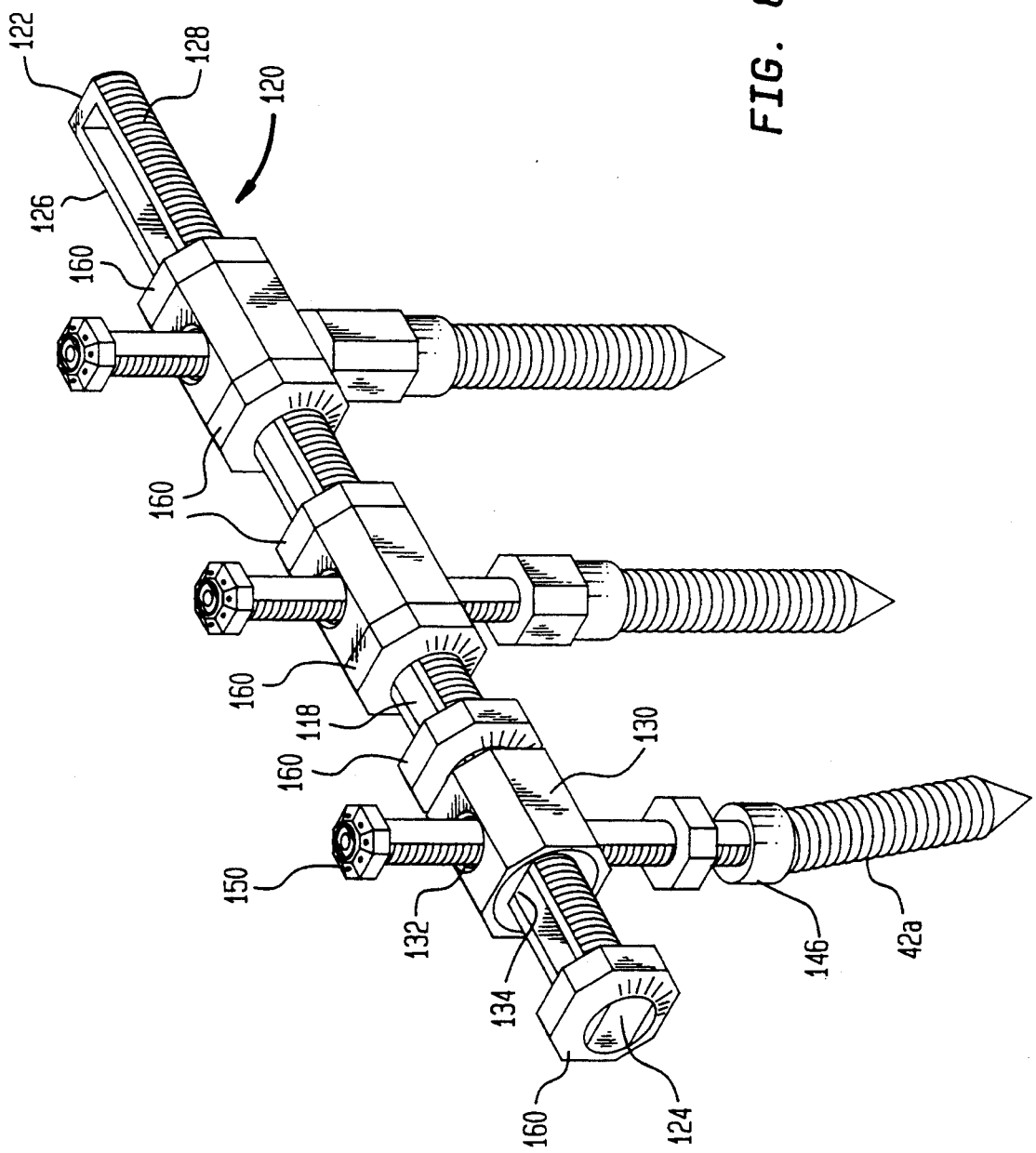
FIG. 8 is perspective view of the embodiment of FIG. 6.

Although the post members 42 illustrated in FIG. 2 are substantially vertical, it is also contemplated, as shown, for example, in FIGS. 3 and 8, to provide posts 42a which are longitudinally "bent" at the shoulder portion, i.e., at angles of between about 5-15 degrees from their vertical axis. In a preferred embodiment, in addition to the substantially vertical posts 42 described herein, posts 42a are provided having a longitudinal bend of 5, 10 or 15 degrees. Such bent posts permit (with the use of spacer members as described below) the surgeon to install the device of the invention at locations where rod member 20 is not exactly aligned with the bore holes in the underlying vertebrae, i.e., due to a weakness or deformed condition of the bone.

The fastener assembly 40 also includes a post nut 50 which is tightened on threaded portion 48 of the post member to lock rod member 20 in position. In the preferred embodiment the proximal portion 48 of the post 48 is "shaved" or narrowed on two sides to provide an effective width of about 4 mm (with a corresponding thickness of about 6 mm). The purpose of this shape is three-fold. First, it permits the upper portion of post member 42 to fit smoothly through the slotted portion of rod member 20. Second, once the post is inserted through the slot in the rod member, it promotes stability of the assembly by preventing rotation of the post within the slot. Thirdly, due to its threaded configuration, it permits the use of a lock nut (as described below) to bind the assembly together.

Beveled recesses are provided on opposite surfaces of the block nut member around the vertical bore 32, and corresponding beveled surfaces are also provided on lock nut 50 and shoulder portion 46 so as to provide a tight fitting engagement which inhibits movement of the rod member relative to the post 42.

As shown in FIG. 3, aperture 49 (preferably 3 mm in diameter) is provided in the proximal end of each post member 42 (and 42a), thus permitting small adjustments to be made to the vertical position of each post through the insertion and movement of a tool (not shown) such as an allen wrench or the like, which also doubles as a handle to facilitate the movement of the post. Aperture 49 may optionally be threaded to more securely engage the adjusting tool. In addition, apertures 52 provided in post nut 50, are configured and adapted for insertion of a stop member such as an allen screw or the like, inserted at an angle for easy placement, which may be utilized if desired to lock nut 50 on threaded portion 48.

The rod members 20 should be able to withstand lateral bending forces and torsion since the system may be used to correct spinal displacement and curvature. However, the rods, block nut members, and fasteners must also be constructed from materials which are biocompatible with human tissue. It will be understood that any materials which possess sufficient strength and biocompatibility may be used in constructing the present invention. Titanium, cobalt chromium surgical implant alloy or strain hardened stainless steel have been found to display suitable strength and biocompatibility characteristics for use in constructing the present invention and are therefore preferred for this purpose.

When two rod assemblies are utilized, e.g., for spinal fixation, a pair of transverse connectors 60 (FIGS. 1 and 4) interconnect the rod members 20. The transverse connectors 60 block relative movement of the rod members so the vertebrae V connected to the rod members are maintained in their desired relative positions and do not pivot relative to an anterior-posterior axis or a longitudinal central axis A of the spinal column. The transverse connectors 60 are located at longitudinally spaced portions of the rod members so that the resulting structure approximates a parallelogram. It will, of course, be apparent that the transverse connectors may be located anywhere along the threaded surfaces of rod members 20.

Figure 4:
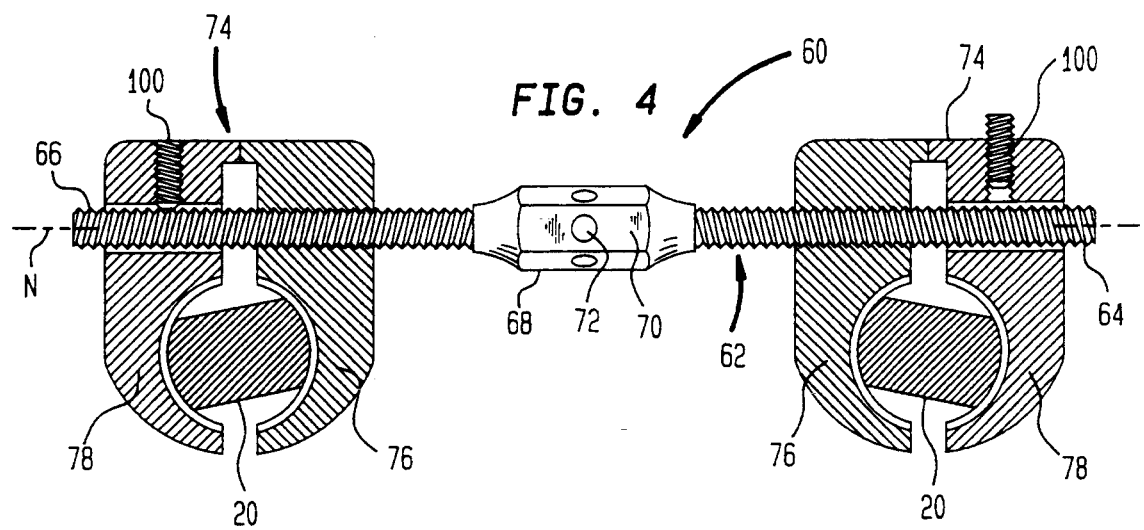
FIG. 4 is an enlarged cross sectional view of the transverse connector for use in joining the slotted rods of the embodiment of FIG. 1, taken approximately along line 4—4 in FIG. 1.

As best seen in FIG. 4, each transverse connector 60 includes an elongate member 62 having a first axial end portion 64 with, for example, a righthand thread and a second axial end portion 66 with an opposed, i.e., lefthand, thread. A drive portion 68 is located intermediate the first and second axial end portions 64 and 66 and receives a suitable tool (not shown) for applying a torque to the member 62 and rotating the member about its longitudinal central axis N in either direction, i.e., clockwise or counterclockwise. The drive portion 68 preferably has a hexagonal shape taken in a plane extending perpendicular to the longitudinal central axis N of the member 62. The drive portion 68 includes diametrically opposite flats 70 which can be engaged by a wrench for rotating the member 62. The drive portion 68 preferably also includes an opening 72 centrally located in each of the flats 70 for receiving a projection from a tool (not shown) with a tapered end adapted for rotating the member 62.

Figure 4A:
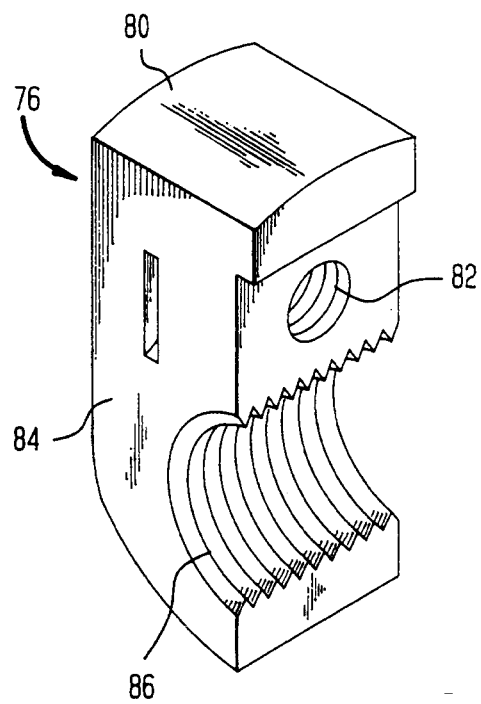
FIG. 4a is an enlarged perspective view of an inner portion of one of the clamp assemblies illustrated in FIG. 4.

The transverse connector 60 also includes a pair of clamp assemblies 74 for attaching the member 62 to the rod members 20. Each of the interchangeable clamp assemblies 74 includes an inner clamp member 76 and an outer clamp member 78. Referring now to FIGS. 4 and 4a, the inner clamp member 76 includes a connector portion 80 with a threaded opening 82 extending therethrough for threaded engagement with one of the threaded end portions 64, 66 of member 62. A body portion 84 is formed integral with and extends from the connector portion 80 of the inner clamp member 76. The body portion 84 is machined to define an arcuate, threaded surface 86. The threaded surface 86 corresponds to the threaded surface of the rod member 20 for locking the member to the rod.

In a preferred embodiment, the inner clamp member 76 for threaded engagement with the threaded end portion 64 has a righthand threaded opening 82, whereas the inner clamp member 76 for threaded engagement with the threaded end portion 66 has a lefthand threaded opening 82. When the member 62 is rotated in one direction about its longitudinal central axis, the inner clamp members 76 are moved axially along the member toward one another. When the member 62 is rotated about its longitudinal axis in the opposite direction, the inner clamp members are moved away from one another.

Figure 4B:
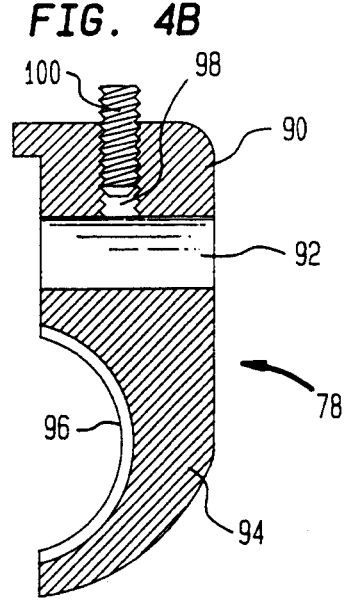
FIG. 4b is an enlarged cross sectional view of an outer portion of one of the clamp assemblies illustrated in FIG. 4.

Each of the clamp assemblies 74 also includes an outer clamp member 78. Referring now to FIG. 4b, each outer clamp member 78 includes a connector portion 90 with a smooth bore 92 extending longitudinally therethrough for receiving a portion of the member 62.

A vertical bore 98 through the surface of connector portion 90 and in communication with the bore 92 permits the introduction of a fastening screw 100 for retention of the outer clamp member 78 relative to end portion 64 or 66. The outer clamp member 78 may be used on either of the threaded end portions 64, 66. A body portion 94 is formed integral with and extends from the connector portion 90 of the outer clamp member 78. The body portion 94 is machined to form an arcuate, threaded surface 96. The threaded surface 96 corresponds to the threaded surface of the rod member 62.

The threaded arcuate surfaces 86 and 96 of the clamps define an axial bore for receiving the threaded rod members 20. To install transverse connector 60, the ends of rod member 62 are inserted within the threaded openings 82 of two inner clamp members 76 and thereafter through the smooth bore 92 of two corresponding outer clamp members 78. Member 62 is then rotated to achieve the desired spacing. Set screw 100 may be tightened within vertical bore 98 to provide added stability of the clamp member with respect to the member 62.

As best seen in FIGS. 3 and 5, the need for bending the rod member 20 to achieve the varying corrective forces at each vertebra required for maintaining or recreating lordosis is obviated by the use of threaded spacers 102 (in combination with the bent posts described above). However, although no longer required, curved rod members (not shown) are available for use with the system of the invention by those surgeons who prefer them. Spacers 102 are mounted between a bone screw shoulder 46 and the rod member 20. Spacers 102 have a vertical bore corresponding to the external diameter of threaded portion 48 of the post member and are of varying length, i.e., thicknesses. Preferably, the spacer bore is threaded to impart rigidity and provides adequate clearance to facilitate quick insertion on threaded portion 48 of a post member. However, the spacer bore may also be smooth if desired.

The upper and lower surfaces of the spacer 102 are preferably beveled in a fashion identical to the beveled surface of the post nut 50. After a spacer is threaded on a post 42 and positioned between rod 20 and shoulder 46, the upper beveled surface of the spacer will be seated in a corresponding block nut member recess and the lower beveled surface of the spacer will be seated in the beveled shoulder recess. It should be apparent that by selecting spacers of incrementally increasing thickness, a sagittal curvature can be achieved without bending the rod members 20. As a result, a predetermined lordosis can be maintained or recreated as desired by selecting spacers of appropriate size. It is also contemplated that combinations of spacers may be employed on the same post member to produce a desired spacing effect in a manner similar to using gage blocks, so that individual spacers of known thicknesses may be combined to produce any desired thickness.

As best shown in FIGS. 1 and 3, an angled end block member 2 may be provided at the lower end of each rod member when the assembly is used for spinal stabilization to facilitate attachment of the fixation device 10 to the sacrum S. End block member 2 comprises a first section 4 which is substantially horizontal and a second section 6 which is angled upwardly from the horizontal plane. An axial threaded bore 8 extends substantially through the center of the section 4. The end block member is threaded onto the end of the rod member 20. Second section 6 is angled upwardly at angle $\theta$ relative to an axis B defined by the axial bore 8 and includes a bore 9 for receiving a bone screw 12 inserted at an angle approximately perpendicular to the sacrum S. Preferably, the system will include several end block members 2 whose angle θ is equal to between 5 and 25 degrees. By selecting an end block member 2 having an appropriate angle θ, and by rotating member 60 so that rod member 20 extends through the axial bore 8 by an appropriate longitudinal distance, the bore 9 will be precisely positioned to retain the sacrum (or "bone") screw 12 in whatever alignment the surgeon desires in three dimensions. This perpendicular alignment minimizes the risk of screw displacement and obviates the necessity of bending rod member 20.

Figure 6:
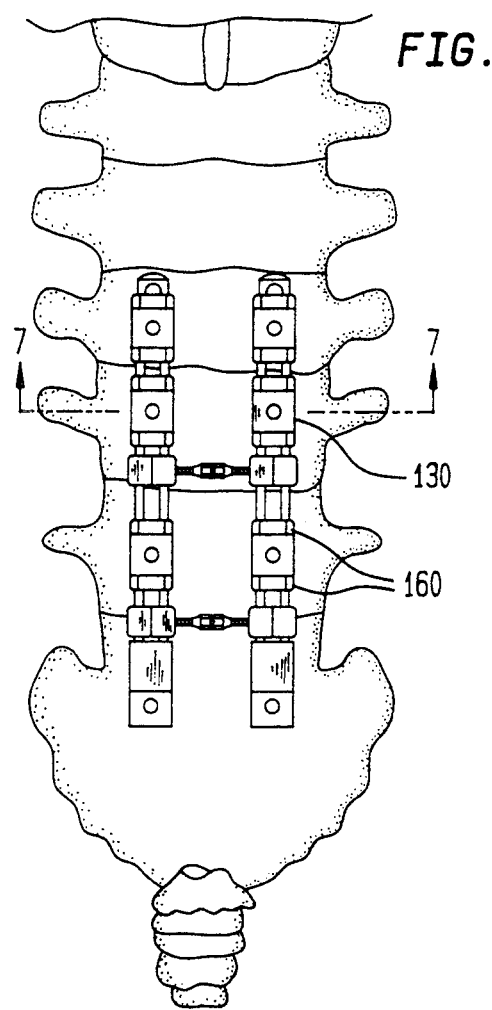
FIG. 6 is a plan view of an alternate embodiment of the present invention.
Figure 7:
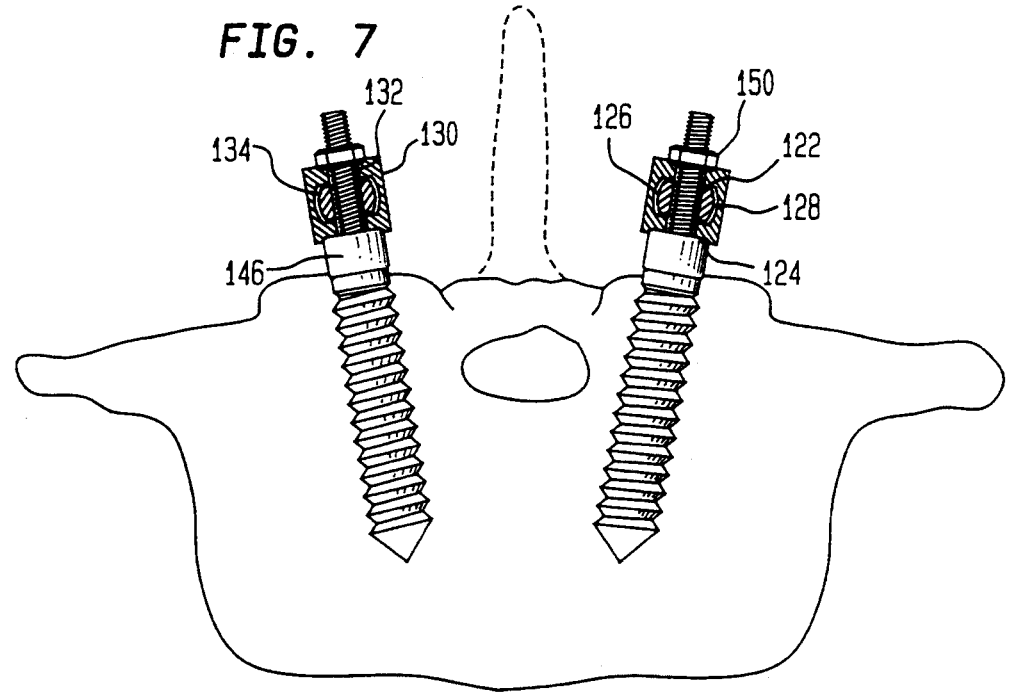
FIG. 7 is an enlarged cross sectional view of the embodiment of FIG. 6 connected to a vertebra, taken approximately along line 7—7 in FIG. 6.

With particular reference to FIGS. 6-8, a second embodiment of the present invention is also described. As shown in FIG. 6, the fixation device of the subject embodiment has a number of features similar to the arrangement shown in FIG. 1. However, in the embodiment of FIGS. 6-8, the axially threaded block nut member is omitted and the fasteners 40 are instead secured by axially slotted block nut members 130. As best seen in FIGS. 7 and 8, each axially slotted block nut member 130 has a threaded vertical bore 132 and a smooth bored axial slot 134. The cross sectional dimensions of axial slot 134 corresponds to the peripheral contour of the rod member 120, as defined by threaded portions 126 and 128 and planar surfaces 122 and 124.

As shown in FIG. 7, there is sufficient clearance between the interior wall of the block nut member 130 and the threaded surface of the rod member 120 to permit sliding movement therealong. Vertical bore 132 remains aligned with slot 118 at all times. Slotted block nut member 130 may be provided with beveled recesses on its upper and lower surfaces in order to receive corresponding bevelled portions of post nut 150 and shoulder 146, respectively. Once the block nut members 130 are positioned in their desired locations, or moved along the threaded rod to create forces of compression and distraction, they are held in place by positioning a pair of threaded traction nuts 160 as shown in FIG. 8. Corresponding faces of traction nuts 160 and the block nut member 130 may be correspondingly bevelled to produce a tight, interlocking engagement.

Figure 9:
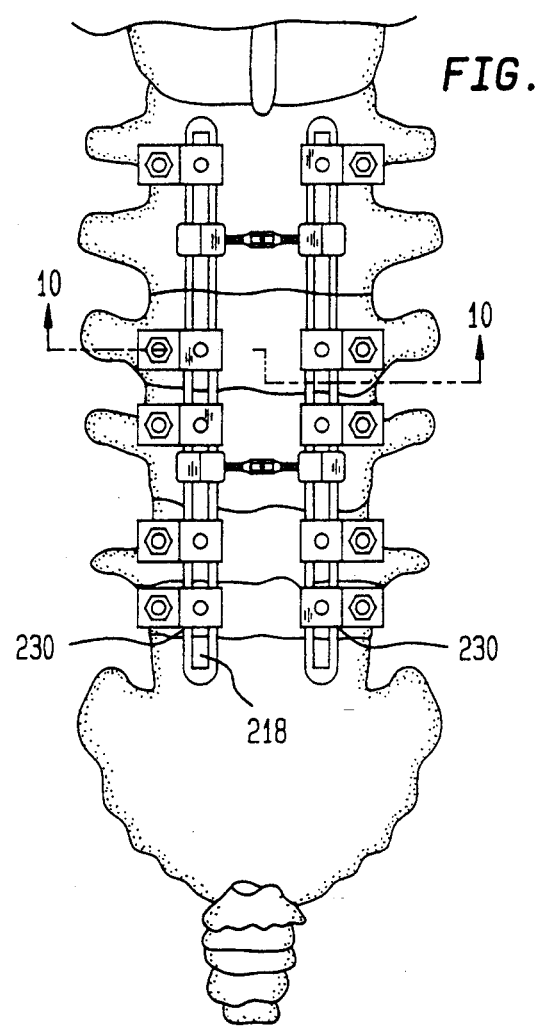
FIG. 9 is a plan view of a further embodiment of the present invention.
Figure 10:
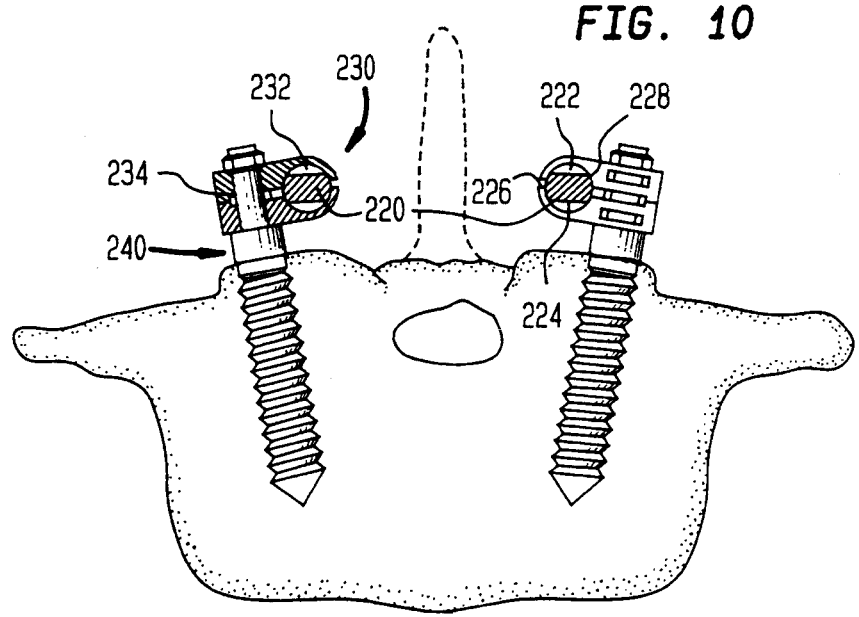
FIG. 10 is an enlarged cross sectional view of the embodiment of FIG. 9, taken approximately along line 10—10 in FIG. 9.

With particular reference to FIGS. 9 and 10, a third embodiment of the present invention is also described. As shown in FIG. 9, the fixation device has many features similar to those of the arrangement shown in FIG. 1. However, in this embodiment, the axially threaded block nut members are omitted and the fasteners 240 are instead secured by axially threaded offset block nut members 230.

Referring now to FIG. 10, each offset block nut member 230 has a threaded axial bore 232 and an offset vertical bore 234. The diameter and thread of axial bore 232 correspond to the diameter and threads of the rod member 220, as defined by threaded portions 226 and 228 and planar surfaces 222 and 224. It will be apparent that by rotating offset block nut member 230, it can be moved along the rod 220 and into any predetermined angular position with respect thereto. Further, rotating the offset blocks permits respective fasteners 240 to be maintained in any desired angular relationship with respect to corresponding pedicles and with respect to each other.

Figure 11:
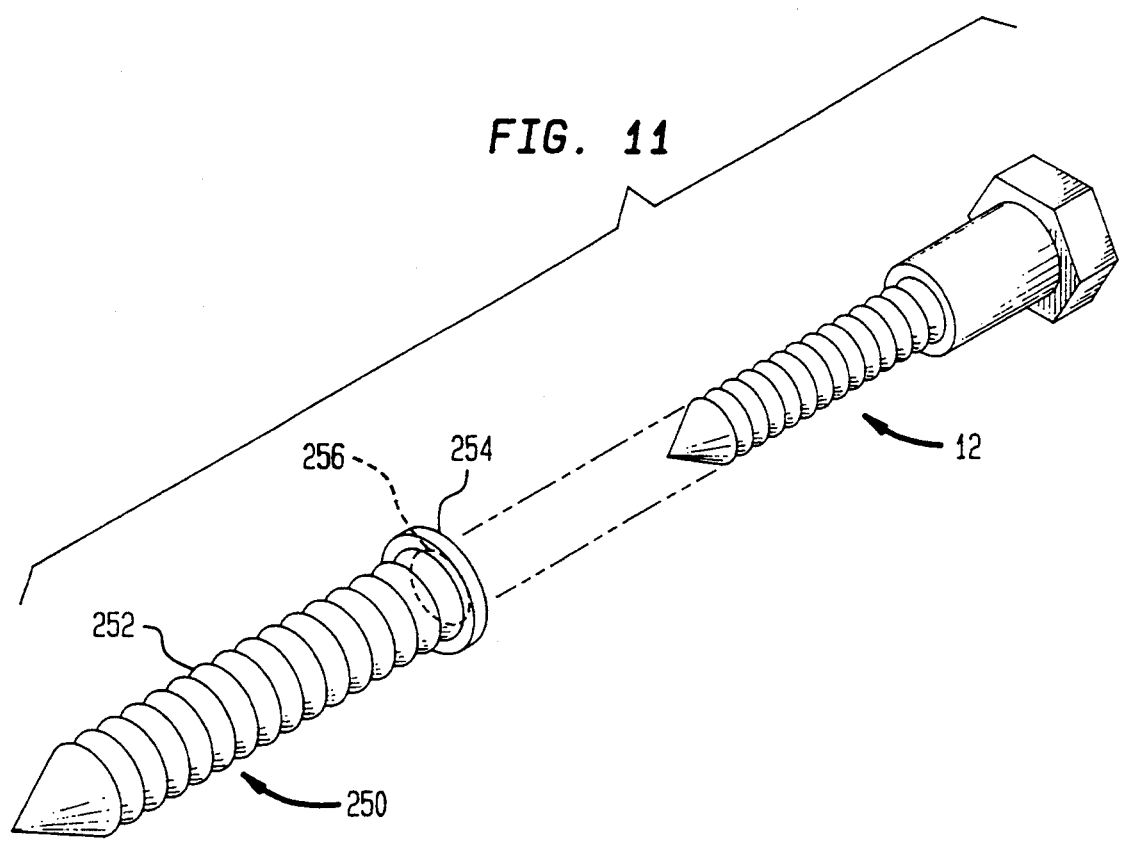
FIG. 11 is a perspective view of a sacrum insert repair set adapted for use with the present invention.

FIG. 11, a illustrates a bore adjustment member for use in making "repairs" to the system of the present invention. Alternatively, this member may, with modifications made as described below, be adapted for use in repairing other (i.e., prior art) fixation devices available for similar applications.

Because of the impact of flexure and torsion due to patient movements and the like, a post for affixing a rod member and one or more slotted or threaded block members to corresponding pedicles, or alternately, a screw for affixing the end block member to the sacrum, may either break or loosen within the bone and thus lose its effectiveness. In either event, it therefore becomes necessary to remove and replace the post or screw in question. In the situation where loosening of a post or screw has necessitated its removal, the prior art requires that the vacated bore be reamed to accommodate a larger fastener. The present invention obviates the reaming of a new hole by the use of bore adjustment member 250, having an augur thread configuration 252 upon its outer surface. The "augur" thread configuration of member 250 permits it to enter the preexisting hole and create a new bore of suitable width as it does so, as in the manner of a "molly" in drywall construction. The upper surface 254, i.e., that closest to the surface of the bone, of member 250 is configured (once member 250 is screwed into the bone) to lie substantially flat upon the surface of the bone.

Member 250 is available in a variety of configurations, i.e., having a threaded axial bore 256 of a pitch and diameter corresponding either to that of a bone screw 12 or a post member 42 or 42a (not shown), depending upon the application desired. Once member 250 is fully augured into the existing hole in the bone, e.g., either the pedicular portion of a vertebrae, or a sacrum, the distal end of a bone screw 12 (or a post member) is threaded into interior bore 256 of member 250.

Thus, when used for example, to repair a loose or broken bone screw 12 for securing an end block member to the sacrum, the fixation device is disassembled, the old bone screw 12 is removed and member 250, adapted and configured for insertion therein of a replacement bone screw, is augured into the sacrum to provide a new support therefor. The fixation device is then reassembled and a new bone screw (or the original screw if it is still intact) is passed through the vertical bore in the end block member and screwed into bore 256 in member 250.

Alternately, when a post member 42 (or 42a) requires repair or replacement, after disassembling the fixation device of the invention, the old post (42 or 42a) is removed and a bore adjustment member 250, configured and adapted for insertion of a post member, is augured into the corresponding pedicle or other bony surface until its upper surface lays flat on the bone. Then, a new (or the original) post member is screwed down into the bore 256 until the post is locked in place. The fixation device is then reassembled in the normal manner as described above.

Moreover, by configuring bore adjustment member 250 in different sizes and/or shapes as necessary to accept the posts and/or screws used for securing the bone segments in other prior art fixation systems available on the market, it is presently contemplated that the apparatus described herein can also have a substantially universal application to any number of prior art fixation devices, thus substantially reducing the surgical difficulties previously encountered in making repairs to such prior art systems.

Although the present invention has been described in connection with the field of stabilization and immobilization of the spine, this is for purposes of general illustration only and it should be readily appreciated by those of ordinary skill in the art that applicants' system may be employed to immobilize other bone segments of the body such as, for example, those of the arm or the leg in the case of, e.g., a compound fracture. Further, it is specifically contemplated that the various elements of each of the disclosed individual embodiments may be used together in a single system.

What is claimed is:

1. A device for stabilizing bone segments, said device comprising:
   at least one elongated rod member, said member defining at least one slotted opening therethrough and having a threaded exterior portion; and
   means for anchoring said at least one rod member to a plurality of bone segments, each said anchoring means comprising
      a post member adapted for engaging one of said bone segments, said post member having a proximal end, a distal end and a shoulder portion located between said proximal and said distal ends, wherein said proximal end is configured for passage through said at least one opening in said rod member and thereafter into a block nut member for securing said post member and said rod member, and wherein said distal end is threaded for insertion into and engagement with one of said bone segments, and further wherein said shoulder portion is adapted for spacing said rod member from said bone segments and is provided upon an upper portion thereof with a bevel adapted to facilitate a substantially locking engagement between said post member and said block nut member;
      a block nut member mounted upon said rod member for securing said rod member relative to said post member, said block nut member defining a bore extending substantially vertically therethrough, said bore configured and adapted to permit passage of at least a portion of said post member proximal end to create an interlocking fit with said post member; and
      at least one spacer member located between said post member shoulder portion and said block nut member, said at least one spacer member configured for controlling the distance between said shoulder portion and a lower surface of said block nut member.

2. A stabilization device according to claim 1 wherein said at least one spacer member is provided with a bevel upon a first and second portion thereof adjacent, respectively, said shoulder and the lower surface of said block nut member, to facilitate a substantially interlocking fit thereamong.

3. A device for stabilizing bone segments, said device comprising:
   at least one elongated rod member, said member defining at least one slotted opening therethrough and having a threaded exterior portion; and
   means for anchoring said at least one rod member to a plurality of bone segments, each said anchoring means comprising
      a post member having a proximal end and a distal end, wherein said proximal end is configured and adapted for insertion through said at least one opening in said rod member and also through a block nut member adapted for securing said elongated rod member relative to said post member, and wherein said post member distal end is threaded for insertion into and engagement with one of said bone segments, and
      a block nut member mounted upon said rod member, said block nut member defining an axial bore extending longitudinally therethrough from a first side to a second side thereof configured and adapted for passage of at least a portion of said elongated rod member therethrough to permit adjustable positioning of said block nut member along said rod member, said block nut member further defining a substantially vertical bore configured for receiving the proximal end of said post member to create an interlocking fit with said post member.

4. A stabilization device according to claim 3 wherein said vertical bore intersects with said axial bore within said block nut member and wherein said vertical bore is alignable with said at least one slotted opening in said rod member.

5. A stabilization device according to claim 3 wherein said vertical bore is offset from said axial bore within said block nut member.

6. A stabilization device according to claim 3 wherein said proximal end of said post member is threaded and wherein said engaging means further comprises means for locking said proximal end of said post member within said substantially vertical bore of said block nut member.

7. A stabilization device according to claim 6 wherein said locking means comprises a post nut adapted for threaded engagement with said proximal end of said post member.

8. A stabilization device according to claim 3 further comprising means for securing said elongated rod to a sacrum, said sacrum securing means comprising an end block member positioned upon a terminal portion of said elongated rod member adjacent said sacrum, said end block member defining a first axial bore configured and adapted for receiving said terminal portion of said elongated rod and a second, substantially vertical bore, spaced apart from said first bore, and adapted for receiving a sacrum engaging screw for securing said end block member to said sacrum.

9. A stabilization device according to claim 8, wherein said first aperture defines a first axis and said second aperture defines a second axis intersecting with said first axis, and wherein said first and second axes intersect at an angle of between about 65 and 90 degrees.

10. A stabilization device according to claim 8 which further comprises a bore adjustment member adapted for repairing means for engaging at least one of said bone segments, said engaging means selected from the group consisting of a post member and a bone screw, said bore adjustment member having a proximal end and a distal end, said distal end provided with an augur thread configuration adapted to create, within said bone segment, a new bore having a width greater than that of said engaging means, said proximal end having a threaded inner axial bore portion therein with a pitch and a diameter corresponding to that of the threaded portion of said engaging means, said engaging means thereafter being screwed into the inner axial bore of the bore adjustment member to provide a locking engagement therebetween.

11. A device for stabilizing a plurality of spinal bone segments, said device comprising:

at least one elongated rod member defining at least one slotted opening therethrough and having a threaded exterior portion;

at least one adjustable block nut member, each said adjustable block nut member having an axial bore extending therethrough from a first side to a second side thereof, configured and adapted to permit adjustable positioning of said block nut member along said elongated rod member; and a substantially vertical bore adapted for engagement with at least a portion of a means for securing said block nut member to a bone segment;

a post member for securing each said adjustable block nut member to a bone segment, each said post member having a proximal and a distal end, said distal end being threaded for insertion into and engagement with a spinal bone segment, said proximal end configured and adapted for insertion through said at least one slotted opening in said elongated rod member and into said substantially vertical bore in a corresponding adjustable block nut member;

a locking member threadably engageable upon a correspondingly threaded portion of the proximal end of each said post member for locking together each said adjustable block nut member with a corresponding post member; and an end block member upon a terminal portion of each said elongated rod adjacent a sacrum portion of said spinal column for securing said elongated rod member to said sacrum, said end block member defining a first axial bore configured and adapted for receiving said terminal portion of said elongated rod and a second substantially vertical bore, spaced apart from said first bore, adapted for receiving a sacrum engaging screw for securing said end block member to said sacrum.

12. A stabilization device according to claim 11 which further comprises a bore adjustment member adapted for repairing means for engaging at least one of said bone segments, said engaging means selected from the group consisting of a post member and a bone screw, said bore adjustment member having a proximal end and a distal end, said distal end provided with an augur thread configuration adapted to create, within said bone segment, a new bore having a width greater than said engaging means, said proximal end having a threaded inner axial bore portion therein with a pitch and a diameter corresponding to that of the threaded portion of said engaging means, said engaging means thereafter being screwed into the inner axial bore of the bore adjustment member to provide a locking engagement therebetween.

13. A stabilization device according to claim 11 which comprises first and second elongated rod members and at least one means for transversely interconnecting said members and thereby maintaining said rod members in a predetermined spatial relation to each other.

14. A device for stabilizing a plurality of spinal bone segments, said device comprising:

at least one elongated rod member defining at least one slotted opening therethrough and having a threaded exterior portion;

at least one adjustable block nut member, each said adjustable block nut member having an axial bore extending therethrough from a first side to a second side thereof, configured and adapted to permit adjustable positioning of said block nut member along said elongated rod member; and a substantially vertical bore adapted for engagement with at least a portion of a means for securing said block nut member to a bone segment;

a post member for securing each said adjustable block nut member to a bone segment, each said post member having a proximal and a distal end, said distal end being threaded for insertion into and engagement with a bone segment, said proximal end configured and adapted for insertion through said at least one slotted opening in said elongated rod member and into said substantially vertical bore in a corresponding adjustable block nut member;

a locking member threadably engageable upon a correspondingly threaded portion of the proximal end of each said post member for locking together each said adjustable block nut member with a corresponding post member;

an end block member upon a terminal portion of each said elongated rod adjacent a sacrum portion of said spinal column for securing said elongated rod member to said sacrum, said end block member defining a first axial bore configured and adapted for receiving said terminal portion of said elongated rod and a second substantially vertical bore, spaced apart from said first bore, adapted for receiving a sacrum engaging screw for securing said end block to said sacrum; and a bore adjustment member interposed between said sacrum engaging screw and said sacrum, said bore adjustment member having a proximal end and a distal end, said distal end provided with an augur thread configuration adapted to permit creation of a new bore in said sacrum having a width greater than that of said sacrum engaging screw, and said proximal end having a threaded inner axial bore portion therein with a pitch and a diameter corresponding to that of a threaded portion of said sacrum engaging screw, said sacrum engaging screw thus being thereafter screwed into said axial bore of said bore adjustment member to provide a locking engagement therebetween.

15. A device for stabilizing bone segments, said device comprising:

(a) first and second fixation assemblies, each said fixation assembly comprising at least one elongated rod member defining at least one slotted opening therethrough and having a threaded exterior portion;

at least one adjustable block nut member, each said adjustable block nut member having an axial bore extending therethrough from a first side to a second side thereof, configured and adapted to permit adjustable positioning of said block nut member along said elongated rod member; and a substantially vertical bore adapted for engagement with at least a portion of a means for securing said block nut member to a bone segment;

a post member for use in securing each said adjustable block nut member to a bone segment, each said post member having a proximal end and a distal end, said distal end being threaded for insertion into and engagement with a spinal bone segment, said proximal end configured and adapted for insertion through said at least one slotted opening in said elongated rod member and into said substantially vertical bore in a corresponding adjustable block nut member;

a locking member threadably engageable upon a correspondingly threaded portion of the proximal end of each said post member for locking together each said block nut member with a corresponding post member; and (b) at least one means for transversely interconnecting said first and second fixation assemblies and thereby maintaining said assemblies in substantially parallel relation to each other.

16. A stabilization device according to claim 15 further comprising means for securing said elongated rod to a sacrum, said sacrum securing means comprising an end block member positioned upon a terminal portion of said elongated rod member adjacent said sacrum, said end block member defining a first axial bore configured and adapted for receiving said terminal portion of said elongated rod and a second, substantially vertical bore, spaced apart from said first bore, and adapted for receiving a sacrum engaging screw for securing said end block to said sacrum.

17. A stabilization device according to claim 16, wherein each said transverse connection means comprises:

an elongate member extendable between said first and said second elongated rod members;

first attachment means for connecting a first terminal portion of said elongate member with said first elongated rod member; and second attachment means for connecting a second terminal portion of said elongate member with said second elongated rod member.

18. A stabilization device according to claim 17 wherein said elongate member comprising a first axial end portion having a left hand thread and a second axial end portion having a right hand thread.

19. A stabilization device according to claim 18 wherein said elongate member further comprises a drive portion located intermediate to said first and said second axial end portions.

20. A stabilization device according to claim 19 wherein said drive portion comprises a plurality of diametrically opposed flats configured for engagement by wrench means for causing rotation thereof.

21. A stabilization device according to claim 20 wherein at least one of said flats defines an aperture, each said aperture being configured and adapted for engagement with tool means adapted for insertion within said aperture to permit rotation of said drive member.

22. A stabilization device according to claim 19 wherein said first and said second attachment means each comprise:

an inner clamp member comprising a connector portion having a threaded bore extending axially therethrough for threaded engagement with a first one of the threaded end portions, and a body portion formed integral with said connector portion, said body portion having, on an inner aspect thereof, a threaded surface corresponding to the threads on said elongated rod member for securing said inner clamp member thereto; and an outer clamp member comprising a connector portion having a substantially smooth bore extending therethrough in alignment with said axial threaded bore in said inner clamp member for engagement with said first end portion of said elongate member, and a body portion formed integral with said connector portion of said outer clamp member, said body portion having, on an inner aspect thereof a threaded surface corresponding to the threads on said elongated rod member for securing said outer clamp member thereto, wherein each said axial end portion is connected, respectively, to both an inner and an outer clamp member through respectively, said threaded and said substantially smooth axial bores thereof such that rotation of said drive portion in a first direction causes said inner and outer clamp members to move toward one another whereas rotation in a second, opposite direction causes them to move apart.

23. A stabilization device according to claim 22 wherein said outer clamp member further includes a set screw for retention of said threaded end portion of said elongate member within said substantially smooth bore.

24. A method for supplying selective angular corrective forces to a plurality of spinal bone segments, said method comprising:

providing a surgical incision on a dorsal surface of a patient adjacent said patient's spinal column;

installing, upon said spinal column, a stabilization device comprising (a) first and second fixation assemblies, each said fixation assembly comprising at least one elongated rod member defining at least one slotted opening therethrough and having a threaded exterior portion;

at least one adjustable block nut member, each said adjustable block member having an axial bore extending therethrough from a first side to a second side thereof, configured and adapted to permit adjustable positioning of said block nut member along said elongated rod member; and a substantially vertical bore adapted for engagement with at least a portion of means for securing said block nut member to a bone segment;

a post member for use in securing each said adjustable block nut member to a bone segment, each said post member having a proximal and a distal end, said distal end being threaded for insertion into and engagement with a spinal bone segment, said proximal end configured and adapted for insertion through said at least one slotted opening in said elongated rod member and into said substantially vertical bore in a corresponding adjustable block nut member;

a locking member threadably engageable upon a correspondingly threaded portion of the proximal end of each said post member for locking together each said block nut member with a corresponding post member, and an end block member located upon a lower terminal portion of each said elongated rod adjacent a sacrum portion of said spinal column for securing said elongated rod member to said sacrum, said end block member defining a first axial bore configured and adapted for receiving said terminal portion of said elongated rod and a second substantially vertical bore, spaced apart from said first bore, adapted for receiving a sacrum engaging screw for securing said end block to said sacrum; and (b) at least one means for interconnecting said first and second fixation assemblies and thereby maintaining said assemblies in substantially parallel relation to each other; and adjusting said stabilization device to provide graded angular movement to said spinal bone segments.

* * * * *